United States Patent
Hoffman (10) Patent No.: US 6,859,514 B2
(45) Date of Patent: Feb. 22, 2005

(54) CT DETECTOR ARRAY WITH UNIFORM CROSS-TALK

(75) Inventor: David M. Hoffman, New Berlin, WI (US)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 95 days.

(21) Appl. No.: 10/249,092

(22) Filed: Mar. 14, 2003

(65) Prior Publication Data

US 2004/0179650 A1 Sep. 16, 2004

(51) Int. Cl.[7] ............................. A61B 6/00; G01T 1/24
(52) U.S. Cl. .................................... 378/19; 250/370.11
(58) Field of Search ...................... 250/368, 370.09, 250/370.11; 378/19, 98.8

(56) References Cited

U.S. PATENT DOCUMENTS

| | | | |
|---|---|---|---|
| 4,161,655 A | 7/1979 | Cotic et al. | |
| 4,414,473 A | 11/1983 | Hoffman et al. | |
| 4,417,144 A | 11/1983 | Hoffman et al. | |
| 4,417,354 A | * 11/1983 | Pfeiler ........................ | 378/19 |
| 4,491,732 A | 1/1985 | Pritzkow et al. | |
| 4,560,877 A | 12/1985 | Hoffman | |
| 4,563,584 A | 1/1986 | Hoffman et al. | |
| 4,686,369 A | 8/1987 | McDaniel et al. | |
| 4,764,679 A | 8/1988 | McDaniel et al. | |
| 4,982,096 A | * 1/1991 | Fujii et al. ................... | 250/367 |
| 5,057,692 A | 10/1991 | Greskovich et al. | |
| 5,585,638 A | 12/1996 | Hoffman | |
| 5,777,390 A | * 7/1998 | Berger et al. ................ | 257/749 |
| 5,799,057 A | 8/1998 | Hoffman et al. | |
| 5,845,003 A | 12/1998 | Hu et al. | |
| 6,087,665 A | 7/2000 | Hoffman et al. | |
| 6,115,448 A | 9/2000 | Hoffman | |
| 6,134,301 A | 10/2000 | Mruzek et al. | |
| 6,137,857 A | 10/2000 | Hoffman et al. | |
| 6,144,718 A | 11/2000 | Hoffman et al. | |
| 6,173,031 B1 | 1/2001 | Hoffman et al. | |
| 6,198,791 B1 | 3/2001 | He et al. | |
| 6,344,649 B2 | 2/2002 | Riedner et al. | |
| 6,389,096 B1 | 5/2002 | Hoffman et al. | |
| 6,437,338 B1 | 8/2002 | Hoffman | |
| 6,445,763 B1 | 9/2002 | Hoffman | |
| 6,448,566 B1 | 9/2002 | Riedner et al. | |
| 6,473,486 B2 | 10/2002 | Hoffman | |
| 6,479,824 B1 | 11/2002 | Hoffman | |
| 6,480,562 B2 | 11/2002 | Jiang et al. | |
| 6,480,563 B2 | 11/2002 | Hoffman et al. | |
| 6,522,715 B2 | 2/2003 | Hoffman et al. | |

* cited by examiner

Primary Examiner—Craig E. Church
Assistant Examiner—Thomas R Artman
(74) Attorney, Agent, or Firm—Ziolkowski Patent Solutions Group, LLC; Michael A. Della Penna; Carl B. Horton (57) ABSTRACT

The present invention is directed to a CT detector array having uniform cross-talk. Discontinuities in cross-talk between adjacent CT detectors of a CT detector array are minimized by increasing the cross-talk at the boundaries of adjacent CT detectors. Discontinuities throughout a CT detector contribute to artifact presence in a final reconstructed image, therefore, it is preferred that cross-talk throughout the CT detector array be relatively uniform. Reducing the width of reflector material between adjacent CT detectors increases the cross-talk between the CT detectors. This increase in cross-talk offsets the reduced cross-talk that typically occurs between scintillators, optical epoxy layers, and photodiodes at the CT detector interface. Cross-talk may also be increased by reducing the amount of chrome deposited in the reflector between CT detectors or reducing the levels of titanium oxide typically used in reflector layers.

18 Claims, 5 Drawing Sheets

CT DETECTOR ARRAY WITH UNIFORM CROSS-TALK

BACKGROUND OF INVENTION

The present invention relates generally to diagnostic imaging and, more particularly, to a CT detector array having uniform cross-talk. More particularly, the invention is directed to a CT array constructed such that the optical cross-talk through the reflector between CT detectors is purposely increased so as to offset reduced electrical cross-talk and coupler layer cross-talk typically present at the interface of CT detectors. Increasing the cross-talk through the reflector between adjacent CT detectors reduces cross-talk discontinuities that contribute to artifact presence in a final reconstructed diagnostic image.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

"Cross-talk" between detector cells of a CT detector is common. "Cross-talk" is generally defined as the communication of data between adjacent cells of a CT detector. Generally, cross-talk is sought to be reduced as cross-talk leads to artifact presence in the final reconstructed CT image and contributes to poor spatial resolution. Typically, four different types of cross-talk may result within a single CT detector. X-ray cross-talk may occur due to x-ray scattering between scintillator cells. Optical cross-talk may occur through the transmission of light through the reflectors that surround the scintillators. Known CT detectors utilize a contiguous optical coupling layer(s), typically epoxy, to secure the scintillator array to the photodiode array. Cross-talk, however, can occur as light from one cell is passed to another through the contiguous layer. Electrical cross-talk can occur from unwanted communication between photodiodes.

Cross-talk between adjacent elements of a CT detector is relatively uniform throughout the single CT detector. However, at the junction of one CT detector to another, there is generally a drop in cross-talk. The drop in cross-talk results from increased reflector material and anti-cross-talk matter disposed between CT detectors or modules as well as reduced electrical cross-talk and coupler layer cross-talk customarily present at the interface or boundaries of adjacent CT detectors. While cross-talk reduction is generally preferred between elements of single CT detector, a drop of cross-talk between CT detectors results in cross-talk discontinuities throughout the CT detector array. These discontinuities negatively affect the final reconstructed image.

Additionally, backlit photodiodes are commonly being used in CT detectors. Backlit diodes are particularly susceptible to electronic cross-talk. As a result, at the interface or junction of CT detectors, there is a greater discontinuity in cross-talk as backlit photodiodes intrinsically are discontinuous in cross-talk at the boundaries of adjacent CT detectors. The implementation of backlit photodiodes, however, is preferred as backlit photodiodes have better tileability and improved interconnectivity than traditional photodiodes.

CT detector array construction typically results in a greater reflector thickness between CT detectors than that found between detector elements of the CT detector. This results in a very finite space that limits the amount of scintillator surface area. If the junction between CT detectors was constructed to match or be less than the width between detector elements of a single CT detector, more of the array space can be devoted to scintillator surface area thereby improving x-ray detection. Additionally, reducing the thickness of reflector material disposed between CT detectors provides improved module to module tolerances for detector manufacturability.

Therefore, it would be desirable to design a CT detector array having uniform cross-talk so as to reduce discontinuities typically found at the interface of adjacent CT detectors. It would also be desirable to design a CT detector array with reduced reflector width between CT detectors thereby improving manufacturing and detector element placement.

BRIEF DESCRIPTION OF INVENTION

The present invention is directed to a CT detector array having uniform cross-talk overcoming the aforementioned drawbacks. Discontinuities in cross-talk between adjacent CT detectors of a CT detector array are minimized by increasing the cross-talk at the boundaries of adjacent CT detectors. Discontinuities throughout a CT detector contribute to artifact presence in a final reconstructed image, therefore, it is preferred that cross-talk throughout the CT detector array be relatively uniform. Reducing the width of reflector material between adjacent CT detectors increases the cross-talk between the CT detectors. This increase in cross-talk offsets the reduced cross-talk that typically occurs between scintillators, optical epoxy layers, and photodiodes at the CT detector interface. Cross-talk may also be increased by reducing the amount of chrome deposited in the reflector between CT detectors or reducing the levels of titanium oxide typically used in reflector layers.

Therefore, in accordance with the present invention, a CT detector array includes a plurality of CT detectors arranged to receive x-rays impinged by a subject and output electrical signals to a data acquisition system. Each of the CT detectors includes a plurality of detector elements. Each element includes a scintillator and a photodiode optically coupled to one another. The CT detectors are aligned relative to one another such that cross-talk throughout the plurality of CT detectors is substantially uniform.

In accordance with another aspect of the present invention, a CT system includes a rotatable gantry having a bore centrally disposed therein. A table is provided and is movable fore and aft through the bore and configured to position a subject for CT data acquisition. A high frequency electromagnetic energy projection source is positioned within the rotatable gantry and is configured to project high frequency electromagnetic energy toward the subject. A detector array is disposed within the rotatable gantry and configured to detect high frequency electromagnetic energy projected thereat and impinged by the subject. The detector array is configured to be absent substantial cross-talk discontinuities.

According to another aspect of the invention, a method of manufacturing a CT detector array includes the steps of forming a plurality of CT detectors in an array and connecting the plurality of detectors to one another such that cross-talk throughout the connected plurality of CT detectors is substantially uniform. Each CT detector includes a plurality of detector elements.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
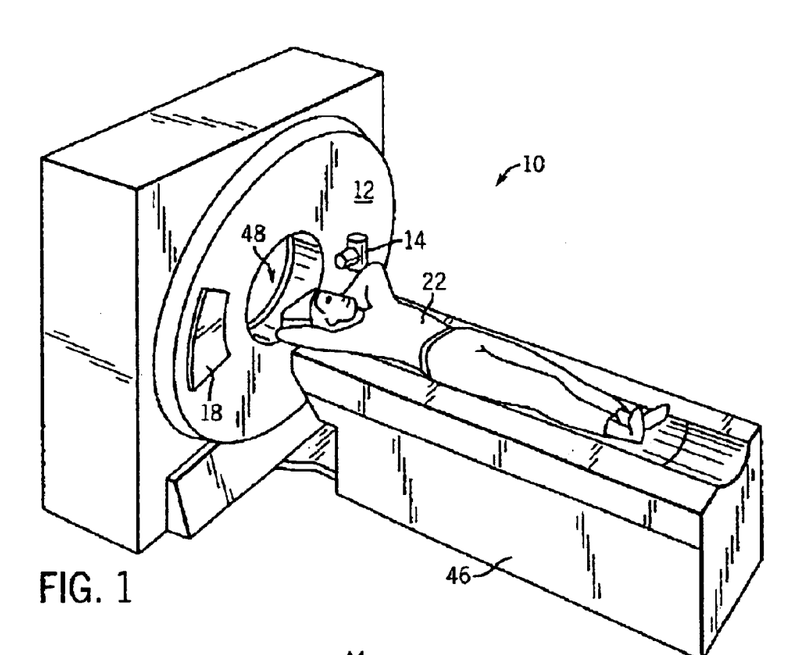
FIG. 1 is a pictorial view of a CT imaging system.
Figure 2:
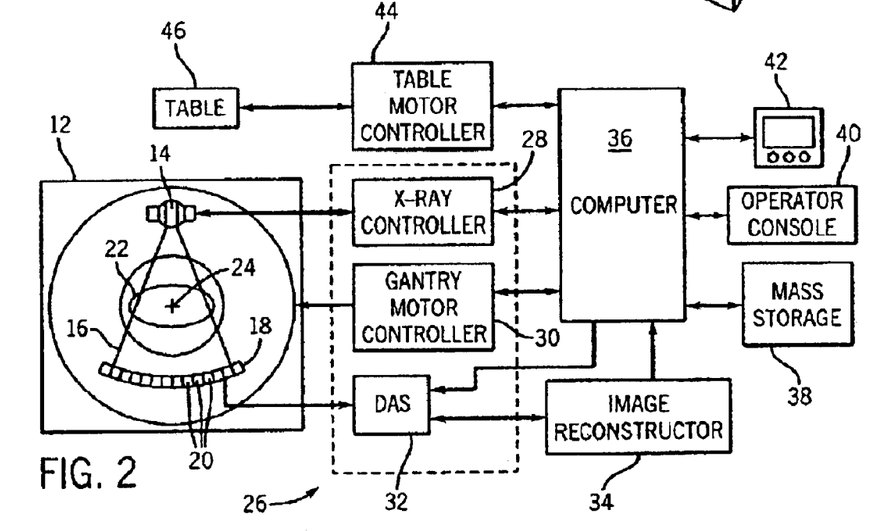
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figures 3, 4:
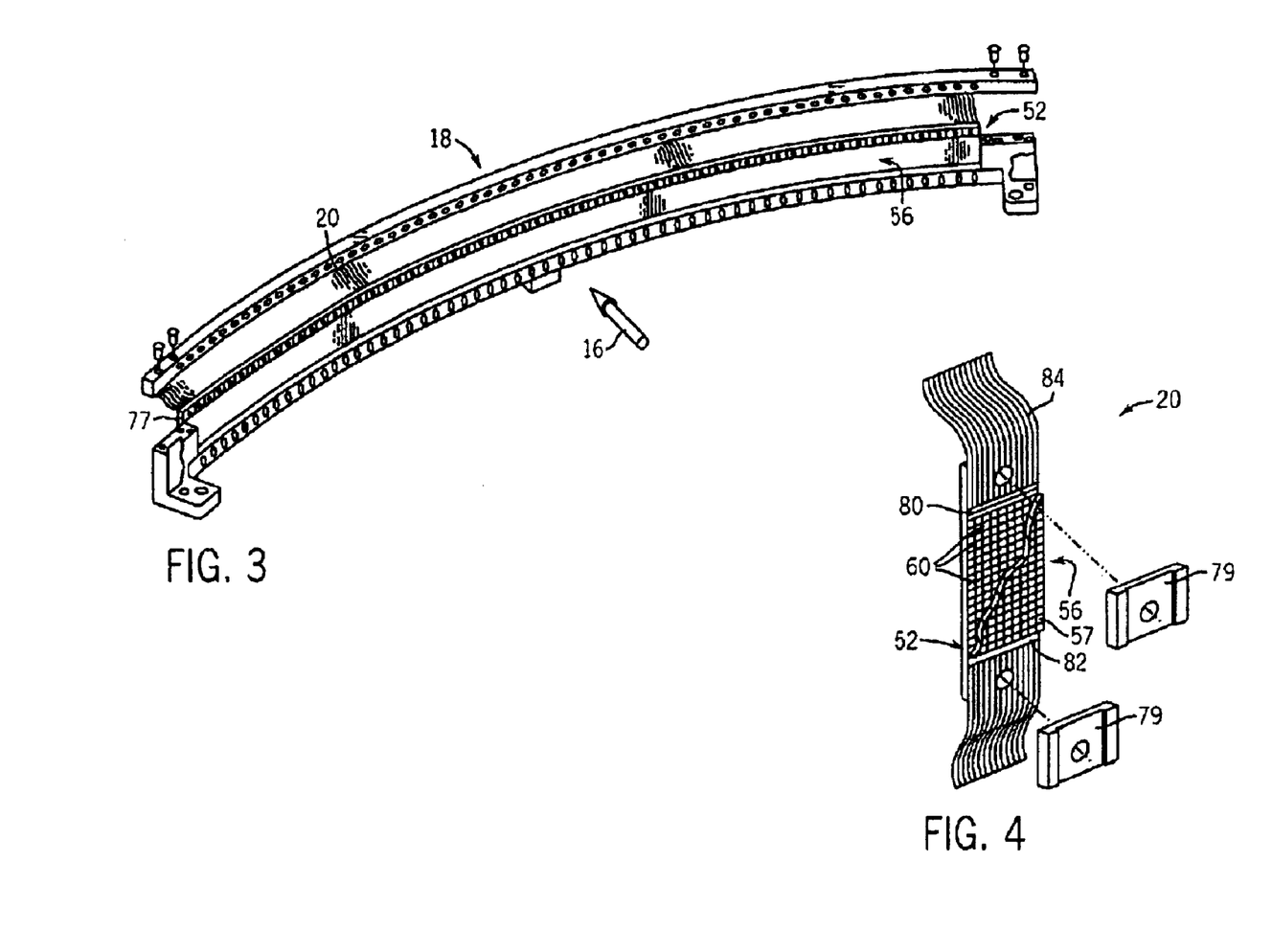
FIG. 3 is a perspective view of one embodiment of a CT system detector array.
FIG. 4 is a perspective view of one embodiment of a detector.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
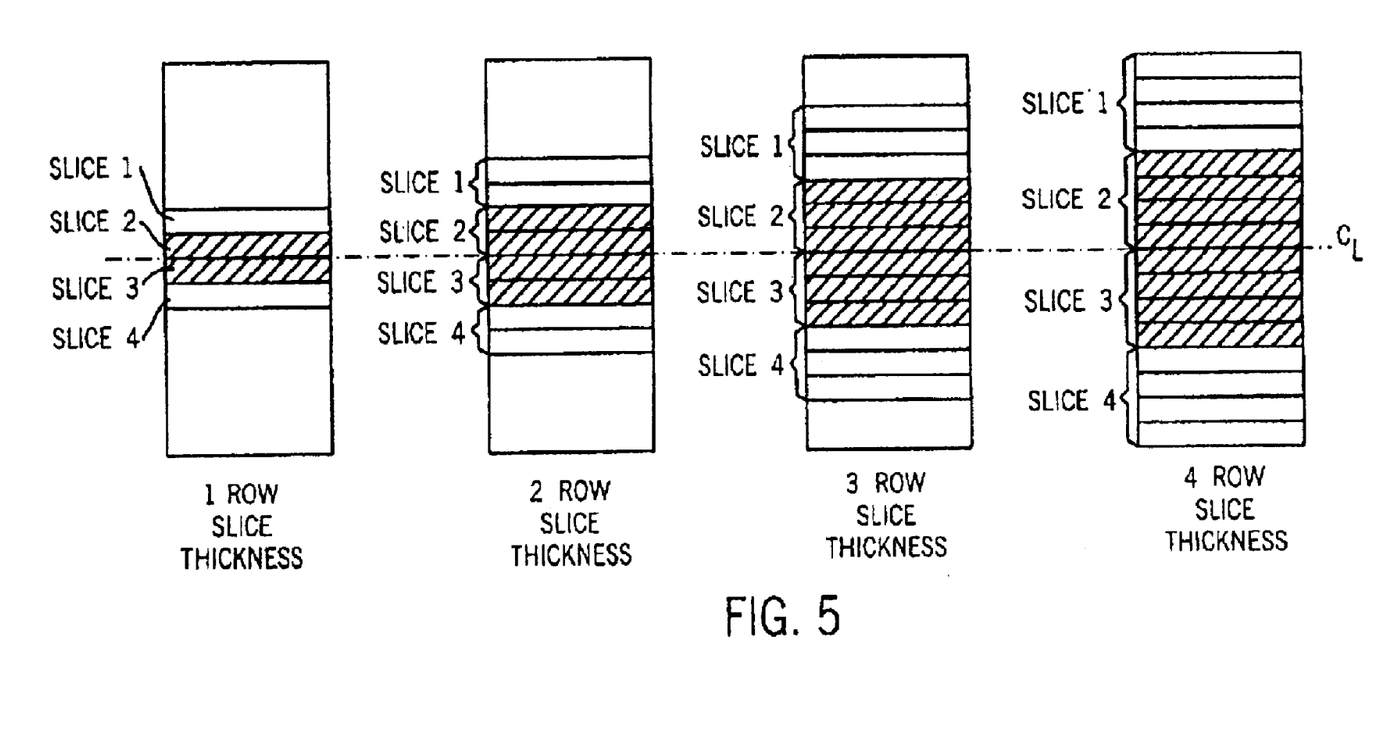
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
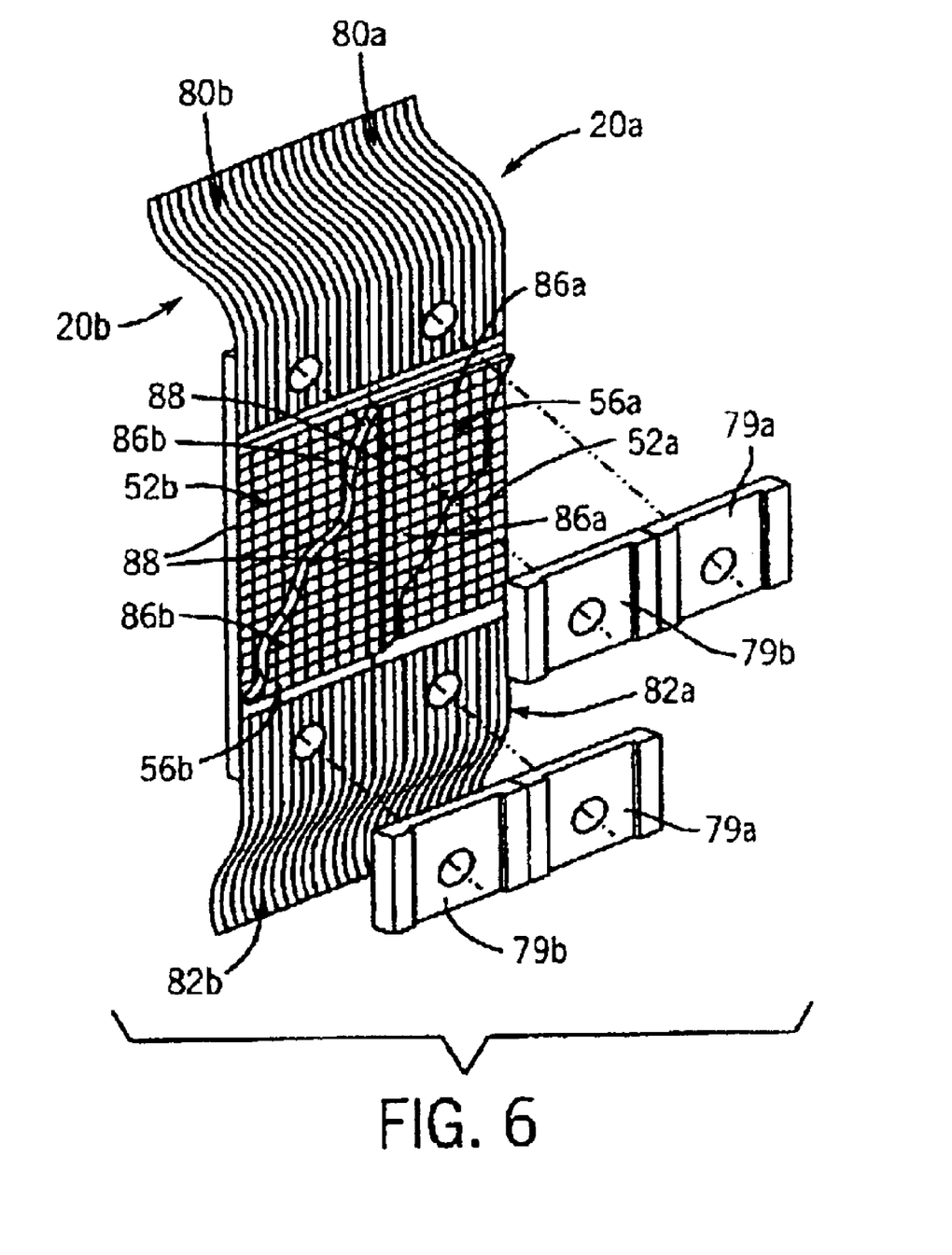
FIG. 6 is a perspective view of adjacent CT detectors of a CT system detector array similar to that shown in FIG. 3.

Referring now to FIG. 6, a pair of adjacent CT detectors is shown. The CT detectors are similar to that which was described with respect to FIG. 4 and, accordingly, like numbers will be used where appropriate. Further, as the construction of each CT detector is similar, suffixes "a" and "b" will be used in the description of the CT detectors of FIG. 6. It should be noted that the illustrated CT detectors comprise only a portion of the CT detector array illustrated and described with respect to FIG. 3.

As shown in FIG. 6, CT detectors 20a, 20b are positioned and aligned relative to one another. Additional CT detectors (not shown) are then used to form a CT detector array, FIG. 3. Each CT detector 20a, 20b is formed of detector elements, each of which includes a scintillator array 56a, 56b and a photodiode array 52a, 52b that are optically coupled to one another via an optically coupling layer (not shown). Reflector elements 86a, 86b are disposed between adjacent scintillators to form a reflector layer. The reflector elements are typically doped with chromium oxide (chrome) to reduce cross-talk emissions and titanium dioxide to improve light reflectivity.

Typically, the CT detectors are formed individually and later aligned and oriented to form a CT detector array. As a result, a reflector element extends along each side of the CT detector. When two CT detectors are then aligned next to one another, a composite reflector wall 88 is formed having a thickness or width that exceeds the width of the reflector elements 86 positioned between adjacent scintillators. This increase in reflector thickness, which is typically doped with anti-cross-talk particles, causes a decrease in cross-talk between CT detector 20a and CT detector 20b relative to the cross-talk between detector elements. For example, the increased reflector width results in larger amount of anti-cross-talk particles, such as chromium oxide, between the CT detectors. The anti-cross-talk particles absorb optical cross-talk introduced in the reflector from each CT detector 20a, 20b. The increased cross-talk absorption together with reduced electrical cross-talk and reduced optical layer cross-talk causes a discontinuity of cross-talk at the interface of adjacent CT detectors.

Reducing the thickness of reflector wall 88 results in a reduction of the number of cross-talk absorption particles between CT detectors. As a result, cross-talk between adjacent CT detectors increases. The reduction in reflector wall 88 thickness is such that the cross-talk between CT detectors is similar to the cross-talk between individual detector elements of a CT detector. The uniformity of cross-talk throughout the CT detector array that results from implementation of a thinner reflector wall 88 between CT detectors minimizes any cross-talk discontinuities which reduce artifacts in the final reconstructed image.

Reducing the thickness of reflector wall 88 is only one example whereupon uniform cross-talk in the CT detector array may be achieved. For example, standard reflector wall 88 thickness may be used but doped with less cross-talk absorption components to increase the cross-talk between CT detectors. Alternately, the amount of titanium dioxide used in the reflector may be reduced such that the reflectivity of reflector wall 88 is reduced. A reduction in the reflectivity characteristics of reflector wall 88 increases cross-talk between detectors.

To achieve a uniform or consistent cross-talk level across the CT detector array, the reflector thickness, reflectivity, and/or cross-talk absorption is controlled such that the amount of cross-talk that results as a result of changes in the reflector between adjacent CT detectors offsets the reduction in optical cross-talk and electrical cross-talk typically experienced between the CT detectors at the boundary or interface of adjacent detectors. Other advantages of this construction include more overall uniform spacing across detector boundaries, increased scintillator area for improved x-ray quantum detection efficiency, generally referenced, "detector QDE". That is, reducing the width of the reflector wall between CT detectors allows for larger scintillator x-ray reception surface. As a result, more x-rays are received by scintillation material and may be used for the imaging process. Thinner reflector elements between adjacent CT detectors also allows for more detector to detector tolerances that improve detector manufacturability.

Figure 7:
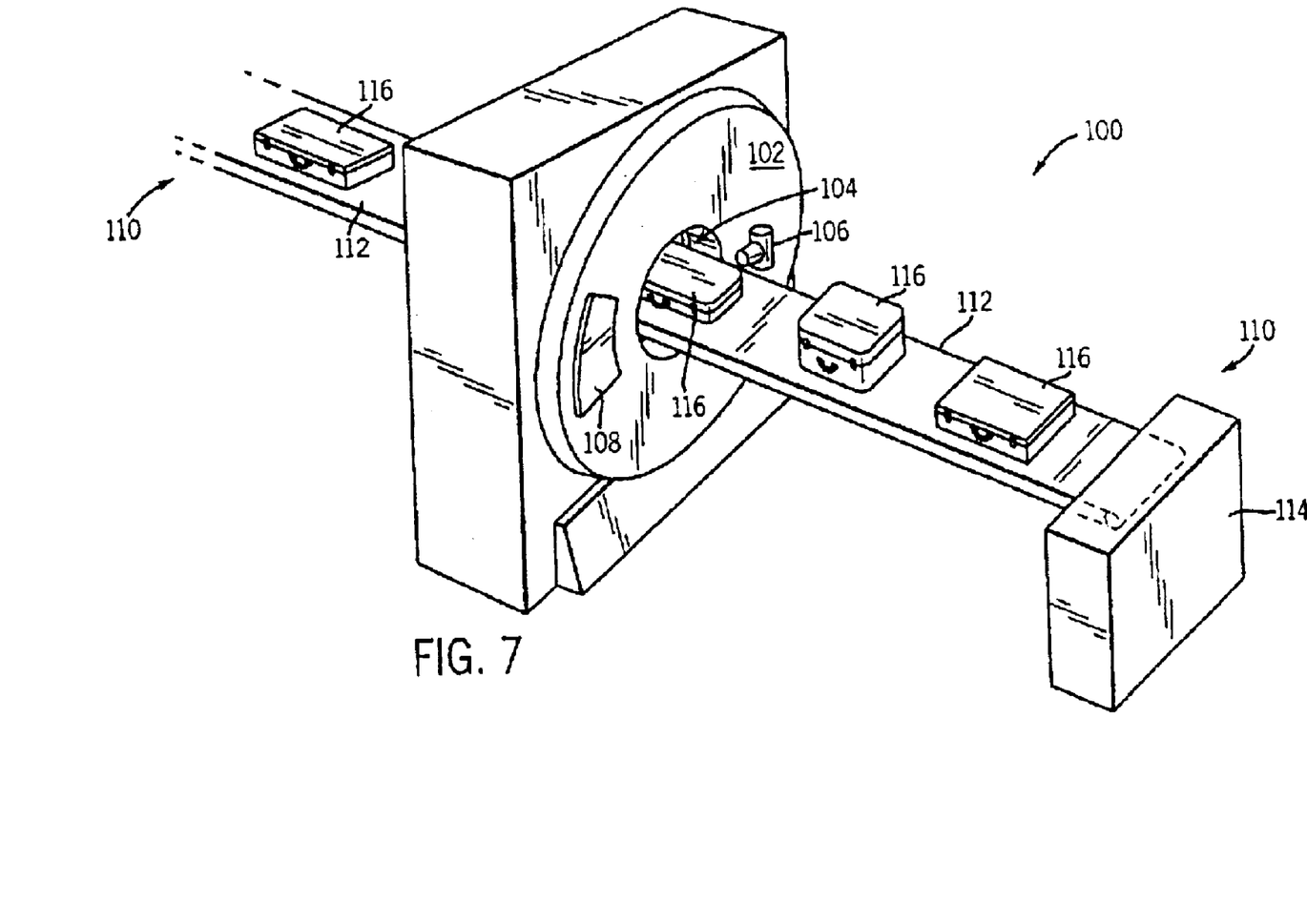
FIG. 7 is a pictorial view of a CT system for use with a non-invasive package inspection system.

Referring now to FIG. 7, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, a CT detector array includes a plurality of CT detectors arranged to receive x-rays impinged by a subject and output electrical signals to a data acquisition system. Each of the CT detectors includes a plurality of detector elements. Each element includes a scintillator and a photodiode optically coupled to one another. The CT detectors are aligned relative to one another such that cross-talk throughout the plurality of CT detectors is substantially uniform.

A CT system includes a rotatable gantry having a bore centrally disposed therein. A table is provided and is movable fore and aft through the bore and configured to position a subject for CT data acquisition. A high frequency electromagnetic energy projection source is positioned within the rotatable gantry and is configured to project high frequency electromagnetic energy toward the subject. A detector array is disposed within the rotatable gantry and configured to detect high frequency electromagnetic energy projected thereat and impinged by the subject. The detector array is configured to be absent substantial cross-talk discontinuities.

A method of manufacturing a CT detector array includes the steps of forming a plurality of CT detectors in an array and connecting the plurality of detectors to one another such that cross-talk throughout the connected plurality of CT detectors is substantially uniform. Each CT detector includes a plurality of detector elements.

The present invention has been described in terms of the preferred embodiment, and it is recognized that equivalents, alternatives, and modifications, aside from those expressly stated, are possible and within the scope of the appending claims.

What is claimed is:

1. A CT detector array comprising:
    a plurality of CT detectors arranged to receive x-rays impinged by a subject and output electrical signals to a data acquisition system;
    each of the CT detectors having a plurality of detector elements, each detector element including a scintillator and a photodiode optically coupled to one another; and
    the CT detectors aligned relative to one another such the cross-talk throughout the plurality of CT detectors is substantially uniform and wherein cross-talk between CT detectors exceeds cross-talk between detector elements.

2. The CT detector array of claim 1 further comprising a reflector element between each adjacent detector element.

3. The CT detector array of claim 2 further comprising a reflector wall between each CT detector.

4. The CT detector array of claim 3 wherein the reflector wall has less thickness than each of the reflector elements.

5. The CT detector array of claim 1 absent substantial cross-talk discontinuities.

6. A CT system comprising:
    a rotatable gantry having a bore centrally disposed therein;
    a table movable fore and aft through the bore and configured to position a subject for CT data acquisition;
    a high frequency electromagnetic energy projection source positioned within the rotatable gantry and configured to project high frequency electromagnetic energy toward the subject; and
    a high frequency electromagnetic energy projection source positioned within the rotatable gantry and configured to project high frequency electromagnetic energy toward the subject; and
    a detector array disposed within the rotatable gantry and configured to detect high frequency electromagnetic energy projected by the projection source and impinged by the subject, the detector array including absent substantial cross-talk discontinuities and including:
        a plurality of CT detectors, each CT detector including a plurality of detector elements; and
        wherein cross-talk between CT detectors exceeds cross-talk between detector elements.

7. The CT system of claim 6 wherein the plurality of CT detectors is separated from one another by a reflector wall having a thickness less than that of a reflector element disposed between adjacent detector elements of each CT detector.

8. The CT system of claim 6 wherein the plurality of CT detectors is separated from one another by a reflector wall fabricated of a material absent chrome.

9. The CT system of claim 6 wherein the plurality of CT detectors is separated from one another by a reflector wall fabricated of a material with reduced $TiO_2$ content.

10. The CT system of claim 6 wherein the substantial cross-talk discontinuities includes optical cross-talk discontinuities.

11. The CT system of claim 6 incorporated into at least one of a mechanical scanner and a parcel inspection apparatus.

12. A method of manufacturing a CT detector array comprising the steps of:
    forming a plurality of CT detectors in an array, each CT detector including a plurality of detector elements;
    forming each detector element by optically coupling a scintillator to a photodiode;
    depositing reflector material between adjacent scintillators;
    forming a reflector wall between adjacent CT detectors, the reflector wall having a thickness greater than that of the reflector material between adjacent scintillators; and
    connecting the plurality of CT detectors to one another such that cross-talk throughout the connected plurality of CT detectors is substantially uniform.

13. The method of claim 12 further comprising the step of disposing a reflector wall between each CT detector, the reflector wall absent chrome.

14. The method of claim 12 wherein the step of connecting further includes the step of affixing the CT detectors to one another such that the array of CT detectors is absent cross-talk discontinuities.

15. The method of claim 12 wherein the step of connecting further includes the step of affixing the CT detectors to one another such that cross-talk between each CT detector is increased relative to cross-talk between the plurality of detector elements of each CT detector.

16. The method of claim 12 wherein the plurality of CT detectors includes a number of backlit photodiode arrays.

17. A method of manufacturing a CT detector array comprising the steps of:
    forming a plurality of CT detectors in an array, each CT detector including a plurality of detector elements; and
    connecting the plurality of CT detectors to one another such that cross-talk throughout the connected plurality of CT detectors is substantially uniform; and
    wherein the step of connecting further includes the step of affixing the CT detectors to one another such that cross-talk between each CT detector is increased relative to cross-talk between the plurality of detector elements of each CT detector.

18. A CT detector assembly comprising:
    a first CT detector module having a first plurality of detector elements separated from one another by a first layer of reflective material;
    a second CT detector module having a second plurality of detector elements separated from one another by a second layer of reflective material; and
    a reflector of reflector material disposed between the first and the second CT detector modules the reflector having a thickness of reflector material thicker than that of the reflective material between detector elements of the first and the second CT detector modules such that cross-talk is substantially uniform across the first and second CT detector modules.

* * * * *

UNITED STATES PATENT AND TRADEMARK OFFICE
CERTIFICATE OF CORRECTION

PATENT NO. : 6,859,514 B2
DATED : February 22, 2005
INVENTOR(S) : David M. Hoffman It is certified that error appears in the above-identified patent and that said Letters Patent is hereby corrected as shown below:

Column 7,
Lines 43-46, delete the second occurrence of "a high frequency electromagnetic energy projection source positioned within the rotatable gantry and configured to project high frequency electromagnetic energy toward the subject; and";
Line 51, delete the word "including";

Column 8,
Line 60, insert -- , -- after "modules".

Signed and Sealed this

Tenth Day of May, 2005

JON W. DUDAS
*Director of the United States Patent and Trademark Office*